United States Patent
Liu (10) Patent No.: US 8,629,178 B2
(45) Date of Patent: Jan. 14, 2014

(54) SODIUM TANSHINONE IIA SULFONATE HYDRATE AND PREPARATION METHOD AND USE THEREOF

(76) Inventor: Li Liu, Foshan (CN)

( * ) Notice: Subject to any disclaimer, the term of this patent is extended or adjusted under 35 U.S.C. 154(b) by 0 days.

(21) Appl. No.: 13/505,878

(22) PCT Filed: Nov. 3, 2010

(86) PCT No.: PCT/CN2010/001761
§ 371 (c)(1),
(2), (4) Date: Jul. 17, 2012

(87) PCT Pub. No.: WO2011/054182
PCT Pub. Date: May 12, 2011

(65) Prior Publication Data
US 2012/0277304 A1    Nov. 1, 2012

(30) Foreign Application Priority Data

Nov. 3, 2009 (CN) .......................... 2009 1 0272663

(51) Int. Cl.
*A61K 31/34* (2006.01)
*C07D 307/77* (2006.01)
(52) U.S. Cl.
USPC .......................................... 514/468; 549/457
(58) Field of Classification Search
USPC ....................................................... 549/457
See application file for complete search history.

(56) References Cited

PUBLICATIONS

Huang, Yu-fang. Journal of Ethnopharmacology 125 (2009) 436-443.*
Byrn, Stephen R. Solid-State Chemistry of Drugs 2nd ed.:Hydrates and Solvates, pp. 233-247 (1999) SSCI, Inc.*
Mingkun Chien et al. Studies on the active principles of dan-shen I. the structure of sodium tanshinone II-A sulfonate and methylene tanshinquinone. Acta Chimica Sinica, 1978, vol. 36, No. 3, pp. 199-205, The whole document.
Zhanjing Yao et al. Study on the sodium tanshinone II a sulfonate and its synthesis technics. Tianran Chanwu Yanjiu Yu Kaifa, 2009, vol. 21, No. 3, pp. 506-508, The whole document.
Journal of Shanghai Jiaotong University, 2007, 27(10):1218-1222.
Chinese Journal of Pathophysiology, 1987, 3:154-158.
The Search Report issued in PCT/CN2010/001761 dated Feb. 10, 2011.
Edited by Xu Shuyun, et al., Pharmacological Test Method, 3rd edition (2001), p. 986-1000.

* cited by examiner

*Primary Examiner* — Noble Jarrell
*Assistant Examiner* — Laura Daniel
(74) *Attorney, Agent, or Firm* — Banner & Witcoff Ltd.

(57) ABSTRACT

The present invention relates to sodium tanshinone IIA sulfonate hydrates as well as preparation methods and uses thereof. The sodium tanshinone IIA sulfonate hydrates have molecular formla of $C_{19}H_{17}NaO_6S \cdot nH_2O$, wherein n=0.5-4.0. The sodium tanshinone IIA sulfonate hydrates of the present invention have better storage stability than anhydrous sodium tanshinone IIA sulfonate.

16 Claims, 5 Drawing Sheets

SODIUM TANSHINONE IIA SULFONATE HYDRATE AND PREPARATION METHOD AND USE THEREOF

The present application is a U.S. National Phase filing of International Application No. PCT/CN2010/001761, filed on Nov. 3, 2010, designating the United States of America and claiming priority to China Patent Application No. 200910272663.8, filed Nov. 3, 2009. The present application claims priority to and the benefit of all the above-identified applications, and all the above-identified applications are incorporated by reference herein in their entireties.

TECHNICAL FIELD

The present invention relates to pharmaceutical technological field. Specifically, the present invention provides a sodium tanshinone IIA sulfonate hydrate useful in treatment of cardio-cerebral vascular disorders. The present invention further relates to a method for preparing the sodium tanshinone IIA sulfonate hydrate of the present invention and use of the sodium tanshinone IIA sulfonate hydrate in the treatment of cardio-cerebral vascular disorders or method thereof.

BACKGROUND ART

Tanshinone IIA is obtained by extraction from Chinese herb dan-shen (salvia miltiorrhiza bunge) (Acta Chimica Sinica, 1978, 3:199-206). Sodium tanshinone IIA sulfonate is obtained by sulfonating tanshinone IIA, this drug has strong water solubility and better therapeutic effects than tanshinone IIA. Sodium tanshinone IIA sulfonate can significantly inhibit the increase of calcium influx caused by high potassium, and has similar effects as convention calcium antagonist Verapamil. Sodium tanshinone IIA sulfonate can significantly reduce spontaneous electric activity on vascular smooth muscle, induce vasodilation, via synergic or combining effects of opening potassium channels of KATP, KCa and blocking calcium channels, thereby having important application value in the treatment of cardio-cerebral vascular diseases. So far, domestic and abroad documents merely report sodium tanshinone IIA sulfonate (tanshinone II Sulfonate sodium, $C_{19}H_{17}NaO_6S$, molecular weight: 396.39), and no document reports sodium tanshinone IIA sulfonate hydrate crystal and preparation method and use thereof.

DESCRIPTION OF THE INVENTION

The inventors of the present invention surprisingly found in research that crystal water-containing sodium tanshinone IIA sulfonate (i.e., sodium tanshinone IIA sulfonate hydrate) has a hygroscopicity far lower than sodium tanshinone IIA sulfonate not containing crystal water, and the crystal water-containing sodium tanshinone IIA sulfonate is more stable than the sodium tanshinone IIA sulfonate not containing crystal water, and thus easy to store and transport, and easy to form water soluble preparations due to its good water solubility at room temperature. In addition, in compared to anhydrous sodium tanshinone IIA sulfonate, the sodium tanshinone IIA sulfonate hydrate of the present invention has good sliding property, improved maneuverability of preparations. Based on the above findings, the inventors of the present invention completed the present invention.

On one aspect, the present invention provides a sodium tanshinone IIA sulfonate hydrate crystal, which molecular formula is $C_{19}H_{17}NaO_6S \cdot nH_2O$, wherein n=0.5-4.0.

In one embodiment, the present invention provides a sodium tanshinone IIA sulfonate hydrate, which molecular formula is $C_{19}H_{17}NaO_6S \cdot nH_2O$, wherein n=0.5-3.0 or n=0.5-2.5.

In one embodiment, the present invention provides a sodium tanshinone IIA sulfonate hydrate, wherein n=2.5.

In another embodiment, the present invention provides a sodium tanshinone IIA sulfonate hydrate, wherein n=1.5.

In another embodiment, the present invention provides sodium tanshinone IIA sulfonate hydrate, wherein n=0.5.

The sodium tanshinone IIA sulfonate hydrate of the present invention can have different crystal forms, for example, the X-ray powder diffraction patterns of sodium tanshinone IIA sulfonate 0.5, 1.5, 2.5, 3.5 hydrates as prepared from methanol-water, ethanol-water or acetone-water crystallization systems or recrystallization systems can be different.

On another aspect, the present invention provides a sodium tanshinone IIA sulfonate 1.5 hydrate having X-ray powder diffraction features.

In one embodiment, the sodium tanshinone IIA sulfonate 0.5 hydrate of the present invention has corresponding characteristic values at the following 2θ: about 3.7, 7.6, 9.0, 9.6, 15.3, 22.0, 26.0, 27.6, 29.8, in a measurement range of diffraction angle 2θ (3-80°) as measured by X-ray powder diffraction method.

In another embodiment, the sodium tanshinone IIA sulfonate 1.5 hydrate of the present invention has corresponding characteristic values at the following 2θ: about 3.7, 6.2, 7.3, 8.8, 9.2, 11.5, 14.7, 15.4, 17, 17.7, 20.6, 21.2, 25.9, 27.1, 27.6, 29.4, in a measurement range of diffraction angle 2θ (3-80°) as measured by X-ray powder diffraction method.

In another embodiment, the sodium tanshinone IIA sulfonate 2.5 hydrate of the present invention has corresponding characteristic values at the following 2θ: about 3.7, 4.3, 6.2, 7.3, 8.8, 9.3, 11.5, 14.7, 15.4, 17, 17.7, 21.2, 25.9, 27.3, 27.6, 29.4, in a measurement range of diffraction angle 2θ (3-80°) as measured by X-ray powder diffraction method.

On another aspect, the present invention provides a method for preparing the sodium tanshinone IIA sulfonate hydrate crystal of the present invention, the method comprising:

Method A: placing tanshinone IIA in a reaction container, adding acetic acid, acetic anhydride, propionic acid, propionic anhydride, C1-C6 low hydrocarbons substituted with halogen, including one or more of dichloromethane, dichloroethane, chloroform, tetrachloroethane, stirring, adding one or more of solutions of acetic acid, acetic anhydride, propionic acid, propionic anhydride in sulfuric acid or fuming sulfuric acid or chlorosulfonic acid, after the end of dropwise adding, stirring at 30° C. or lower for 0.1-6 h, slowly pouring the reactant into water, adding one or more of solutions of sodium chloride, sodium carbonate, sodium bicarbonate, sodium hydroxide (preferably, saturated solutions thereof), precipitating sufficiently, filtering, washing the precipitate once or several times with saturated sodium chloride solution or saturated sodium sulfate solution, then washing once or several times with one or more of water or C1-C6 low molecular weight alcohols including methanol, ethanol, isopropanol, filtering, removing the residual sodium hydrochloride with anhydrous ethanol refluxing, concentrating, subjecting the resultant solid to crystallization with water, C1-C6 low molecular weight alcohols including methanol, ethanol, isopropanol, etc., C3-C6 low ketones including acetone, butanone, hexone, etc., C2-C8 low esters including butyl acetate, ethyl acetate, ethyl formate, etc., C1-C6 low hydrocarbons substituted with halogen, including dichloromethane, dichloroethane, chloroform, etc., C2-C6 low ethers including ethyl ether, methyl ethyl ether, isopropyl ether, etc., C5-C10 straight or branched alkanes or cycloalkanes including pentane, n-hexane, petroleum ether, cyclohexane, etc., aromatic hydrocarbons including one or more of benzene, toluene, etc., standing, cooling, filtering after crystal precipitation, drying to obtain sodium tanshinone IIA sulfonate hydrate crystal, and this crystallization procedure can be repeated once or several times to obtain a product with much high purity; or Method B: placing tanshinone IIA in a reaction container, adding acetic acid, acetic anhydride, propionic acid, propionic anhydride, C1-C6 low hydrocarbons substituted with halogen, including one or more of dichloromethane, dichloroethane, chloroform, tetrachloroethane, stirring, adding a chlorosulfonic acid solution in C1-C6 low hydrocarbons substituted with halogen, including one or more of dichloromethane, dichloroethane, chloroform, tetrachloroethane, after the end of dropwise adding, stirring at 30° C. or lower for 0.1-6 h, slowly pouring the reactant into water, separating organic layer, adding one or more of saturated solutions of sodium chloride, sodium carbonate, sodium bicarbonate, sodium hydroxide to the resultant aqueous solution layer, standing, precipitating sufficiently, filtering, washing the precipitate once or several times with saturated sodium chloride solution or saturated sodium sulfate solution, then washing once or several times with one or more of water or C1-C6 low molecular weight alcohols including methanol, ethanol, isopropanol, filtering, subjecting the resultant solid to crystallization with water, C1-C6 low molecular weight alcohols including methanol, ethanol, isopropanol, etc., C3-C6 low ketones including acetone, butanone, hexone, etc., C2-C8 low esters including butyl acetate, ethyl acetate, ethyl formate, etc., C1-C6 low hydrocarbons substituted with halogen, including dichloromethane, dichloroethane, chloroform, etc., C2-C6 low ethers including ethyl ether, methyl ethyl ether, isopropyl ether, etc., C5-C10 straight or branched alkanes or cycloalkanes including pentane, n-hexane, petroleum ether, cyclohexane, etc., aromatic hydrocarbons including one or more of benzene, toluene, etc., standing, cooling, filtering after crystal precipitation, drying to obtain sodium tanshinone IIA sulfonate hydrate crystal, and this crystallization procedure can be repeated once or several times.

In one embodiment, the solvent used for crystallization or recrystallization of sodium tanshinone IIA sulfonate hydrate crystal is preferably one or more of water, methanol, ethanol, isopropanol, acetone, butone, hexone, methyl acetate, ethyl acetate, dichloromethane, chloroform, ethyl ether, isopropyl ether, petroleum ether and benzene.

The drying for the product of the present invention can be performed under conditions of different temperatures (e.g., 20-100° C.), drying time (1 h to several days), or with additional drying agents (including silica gel, phosphorus pentoxide, anhydrous calcium chloride, anhydrous sodium sulfate, etc.), or using normal pressure or reduced pressure to dry the final product. The drying temperature is preferably at 60° C. or lower.

On further another aspect, the present invention provides a pharmaceutical composition, comprising the sodium tanshinone IIA sulfonate hydrate of the present invention, and a pharmaceutically acceptable carrier.

In one embodiment, the pharmaceutical composition of the present invention is prepared to form frozen dried powder for injection, aseptically subpackaged powders for injection, infusion solutions, small volume injections and preparations for administration via gastrointestinal tract, etc.

The oral preparations include tablets, capsules, granules, which can comprise pharmaceutically acceptable fillers, such as starch, modified starch, lactose, microcrystalline cellulose, cyclodextrin, sorbitol, mannitol, calcium phosphate, amino acids, etc.; the pharmaceutically acceptable disintegrants, such as starch, modified starch, microcrystalline cellulose, sodium carboxymethyl starch, cross-linked polyvinylpyrrolidone, low-substituted hydroxypropyl cellulose, surfactants; pharmaceutically acceptable wetting agents and adhesives, such as gelling starch, methyl cellulose, carboxymethyl cellulose, ethyl cellulose, polyvinylpyrrolidone, alginic acid and salts thereof; pharmaceutically acceptable lubricants and glidants, such as stearic acid, magnesium stearate, polyethylene glycol 4000-8000, talc powder, micronized silica, magnesium dodecylsulfate, etc.; pharmaceutically acceptable sweetening agents and flavoring agents, such as aspartame, sodium cyclamate, saccharin sodium, trichlorosucrose, edible essences, etc.

The sodium tanshinone IIA sulfonate hydrate of the present invention can be processed to form froze-dried powder injections, for example, via the following method: providing sodium tanshinone IIA sulfonate hydrate, optionally adding pharmaceutically acceptable auxiliary solvent, frozen-drying support agent or excipient, stabilizer, injection water, stirring for dissolution, if necessary, adding pharmaceutically acceptable acid/alkali to adjust pH to 3.5-8.5, adding activated carbon 0.005-0.5% (W/V), stirring for 15-45 min, filtering, supplementing water, aseptically filtering, subpackaging 5-80 mg/bottle (expressed in main drug), frozen-drying, tamponing to obtain finished product.

The sodium tanshinone IIA sulfonate hydrate of the present invention can further be processed to form small volume injections, for example, via the following method: adding to the sodium tanshinone IIA sulfonate hydrate with injection water and pharmaceutically acceptable additives, for examples: pharmaceutically acceptable pH adjusters, pharmaceutically acceptable antioxidants, inert gases, filtering, sterilizing to obtain sterilized small volume injections with a pH value of 3.5-8.5.

The pharmaceutically acceptable frozen-drying support agent or excipient can include one or more of lactose, glucose, mannitol, sorbitol, xylitol, dextran, amino acids or salts thereof (including glycine, taurine, arginine, etc.), sodium dihydrogen phosphate, disodium hydrogen phosphate, sodium deoxycholate, etc.

The pharmaceutically acceptable pH adjusters can be pharmaceutically acceptable inorganic acids or organic acids, inorganic alkalis or organic alkalis, and can be wider sense Lewis acids or alkalis, can contain one or more thereof, can be one or more of hydrochloric acid, phosphoric acid, propionic acid, acetic acid and acetate, such as sodium acetate, etc., lactic acid and pharmaceutically acceptable lactates, pharmaceutically acceptable citrates, sodium carbonate, sodium bicarbonate, potassium hydrogen carbonate, sodium hydroxide, potassium hydroxide, phosphates, tartaric acid and pharmaceutically acceptable salts thereof, borax, boric acid, succinic acid, hexanoic acid, adipic acid, fumaric acid, maleic acid, trihydroxyaminomethane, diethanolamine, ethanolamine, isopropanolamine, diisopropanolamine, 2-amino-2-(hydroxymethyl)-propan-1,3-diolamine, hexan-1,2-diamine, N-methylglucosamine, diisopropylamine and salt thereof, polyhydroxycarboxylic acids and pharmaceutically acceptable salts thereof, such as glucuronic acid, glucanic acid, lactobionic acid, malic acid, threonic acid, glucoheptonic acid, amino acids and amino acid salts, etc.

The pharmaceutically acceptable antioxidants and stabilizers can be one or more of sulfurous acid, sulfites, bisulfites, metabisulfites, dithionites, thiosulfates, organic sulfur compounds, such as thiourea, glutathione, dimercaptopropanol, thioglycolic acid and salts thereof, thiolactic acid and salts thereof, thiodipropionic acid and salts thereof, phenol compounds, such as gallic acid and salts thereof, caffeic acid, caffeiates, ferulic acid, ferulates, di-tert-butyl-p-phenol, 2,5-dihydroxybenzoic acid, 2,5-dihydroxybenzoates, phenol or derivatives, salicylic acid and salts thereof; amino acids and salts thereof; ascorbic acid and ascorbates, isoascorbic acid and isoascorbates, nicotinamide, tartaric acid, nitrate, phosphates, pharmaceutically acceptable acetates, citrates, EDTA and EDTA salts, such as EDTA disodium, EDTA tetrasodium, N-bis(2-hydroxyethyl)glycine, α-cyclodextrin, β-cyclodextrin, γ-cyclodextrin, glucosyl-cyclodextrin ($G_1$-CYD), maltosyl-β-cyclodextrin, hydroxypropyl-β-cyclodextrin, 2-hydroxypropyl-β-cyclodextrin (2-HP-β-CYD), 3-hydroxypropyl-β-cyclodextrin (3-HP-β-CYD), sulfobutyl ether-β-cyclodextrin (SBE-β-CD), such as ($SBE_7$-β-CD), $SBE_4$-β-CD, etc.

The pharmaceutically acceptable auxiliary solvents can be one or more of glucose, xylitol, sorbitol, mannitol, nicotinamide, N-methylglucosamine, N-ethylglucosamine, phosphoric acid and pharmaceutically acceptable phosphates (can be sodium dihydrogen phosphate, disodium hydrogen phosphate, sodium phosphate, potassium dihydrogen phosphate, etc.), lactic acid, sodium lactate, citric acid, sodium citrate, polyhydroxycarboxylic acids and pharmaceutically acceptable salts thereof (such as glucuronic acid, glucanic acid, lactobionic acid, malic acid, threonic acid, glucoheptonic acid or pharmaceutically acceptable salts thereof), amino acids and amino acid salts (can be arginine hydrochloride, lysine hydrochloride, etc.), hydrochloric acid, sulfuric acid, tartaric acid, Tween 20-80, poloxamers (including poloxamers 124, 188, 237, 338, 407, etc.), polyethylene glycol 200-2000, ethanol, ethylene glycol, glycerol, glucosyl-cyclodextrin ($G_1$-CYD), maltosyl-β-cyclodextrin, hydroxypropyl-β-cyclodextrin, 2-hydroxypropyl-β-cyclodextrin (2-HP-β-CYD), 3-hydroxypropyl-β-cyclodextrin (3-HP-β-CYD), sulfobutyl ether-β-cyclodextrin (SBE-β-CD), such as ($SBE_7$-β-CD), $SBE_4$-β-CD, and water, etc.

The pharmaceutically acceptable isosmotic adjusters can be one or more of glucose, fructose, xylitol, sorbitol, mannitol, inverted sugars, maltose, dextran, sodium chloride, potassium chloride, sodium lactate, etc.

The sodium tanshinone IIA sulfonate hydrate of the present invention can be used as calcium antagonist in prophylaxis or treatment of coronary heart disease, angina pectoris, myocardial infarction, arrhythmia, ischemic brain diseases, including cerebral thrombosis, cerebral embolism; distal circulation disorders such as various arterial occlusions, angiitis, microcirculation disturbance caused by diabetes, hypertension, hyperlipidemia, etc. in human and mammals.

On another aspect, the present invention provides a use of the sodium tanshinone IIA sulfonate hydrate of the present invention in the manufacture of a medicament, the medicament is useful in treatment or prophylaxis coronary heart disease, angina pectoris, myocardial infarction, arrhythmia, ischemic brain diseases, distal circulation disorders including various arterial occlusions, angiitis, microcirculation disturbance caused by diabetes, hypertension, hyperlipidemia in human and mammals.

Alternatively, the present invention provides a method of treatment or prophylaxis of the above diseases by using the sodium tanshinone IIA sulfonate hydrate of the present invention, comprising: administering a subject in need thereof with a prophylactically or therapeutically effective amount of the sodium tanshinone IIA sulfonate hydrate of the present invention.

Dosage and usage: in general, for an adult, intramuscular injection: 5-80 mg per time, 1-2 times per day. Intravenous injection: 5-80 mg per time, diluted with 20 ml of 25% glucose injection. Intravenous drop: 5-80 mg, diluted with 250-500 ml of 5% glucose injection solution or 0.9% sodium chloride injection solution, 1-2 times per day. For a child, use half or less of the above dosages. Dosage and usage for administration via gastrointestinal tract: for a human or animal with body weight of 10-70 kg, 10-200 mg per day in general, administered in 1-3 batches; for a child, use half or less of the above dosage.

The hygroscopicity test performed according to the Pharmacopoeia of the People's Republic of China (2005 Edition) confirmed that the sodium tanshinone IIA sulfonate hydrate of the present invention is much lower than anhydrous sodium tanshinone IIA sulfonate.

In addition, the accelerated stability test performed according to the Pharmacopoeia of the People's Republic of China (2005 Edition) confirmed that the sodium tanshinone IIA sulfonate hydrate crystal had better storage stability than anhydrous sodium tanshinone IIA sulfonate, and thus can be stably stored for a more longer period.

The sodium tanshinone IIA sulfonate hydrate of the present invention is a red or brick-red or brownish red crystalline powder. Other than requiring air isolation to avoid adhesion due to deliquescence in processing anhydrous sodium tanshinone IIA sulfonate, the sodium tanshinone IIA sulfonate hydrate crystal of the present invention has good sliding property, thereby improving the maneuverability of preparations; and the obtained solid preparations have good dissolution property so that they can be easily absorbed and enter into blood circulation, improve bioavailability and facilitate their quick onset.

SPECIFIC MODELS FOR CARRYING OUT THE INVENTION

Method of Thermal Analysis

Assay condition: Setsys 16, NETZSCH STA449C, from Setaram Company, sample amount: about 5 mg, temperature slope rate: 10 K/min, $N_2$ flow rate: 50 ml/min, temperature: room temperature to about 400° C. in general.

Figure 1:
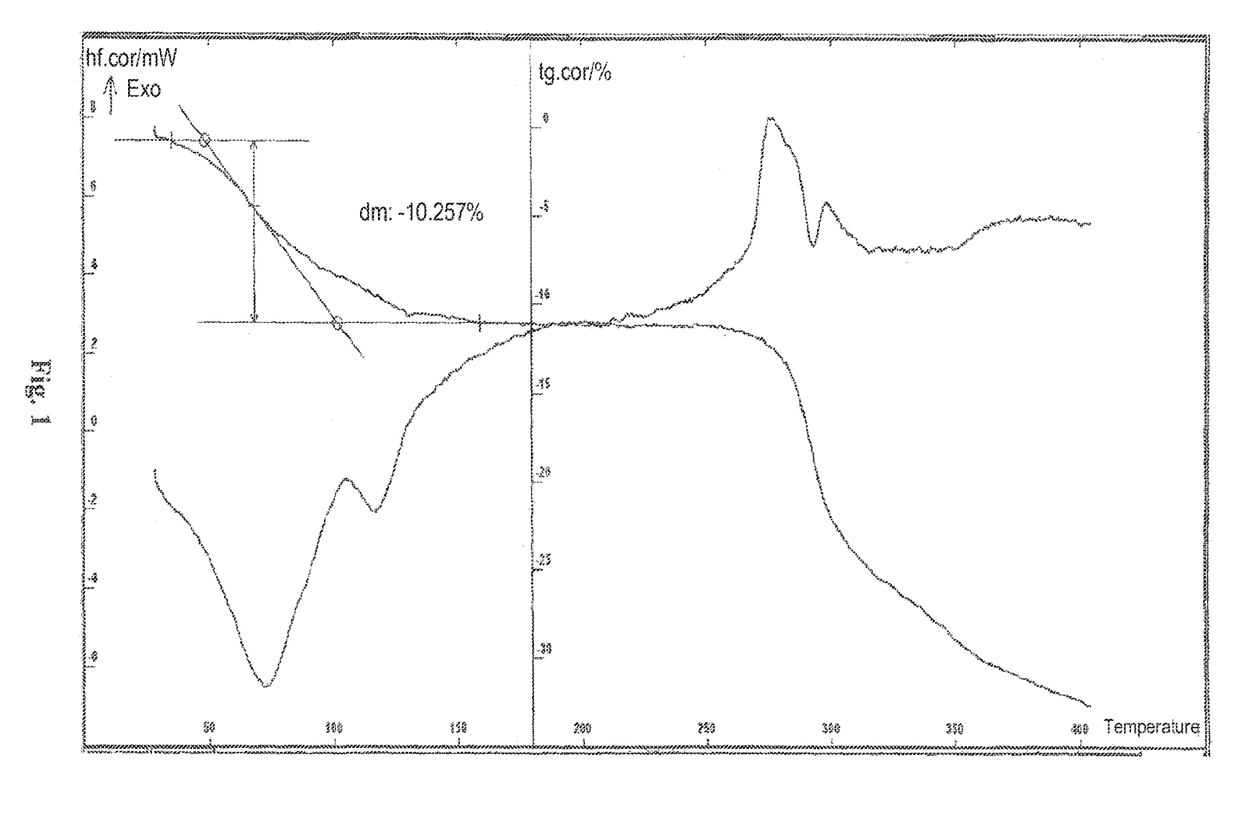
FIG. 1 is a thermogram of sodium tanshinone IIA sulfonate 2.5 hydrate.
Figure 2:
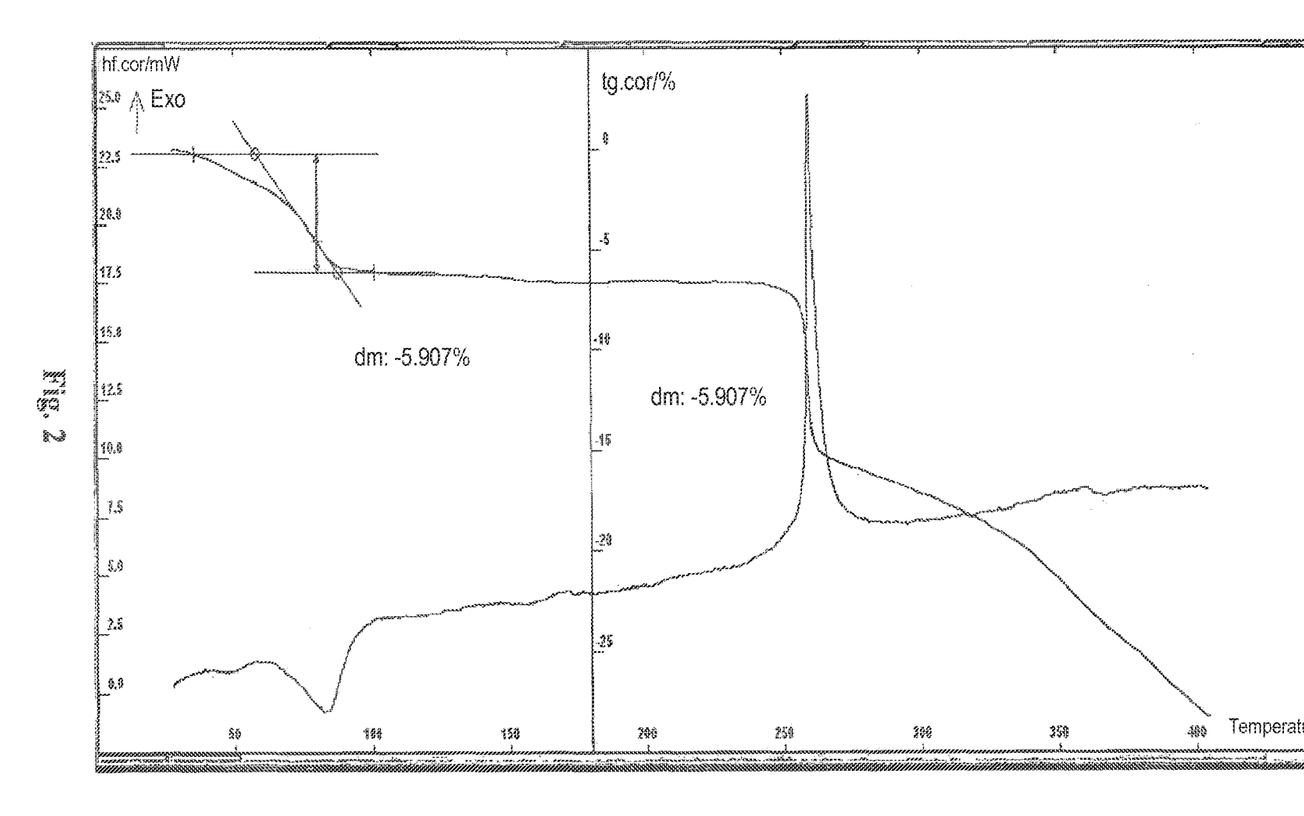
FIG. 2 is a thermogram of sodium tanshinone IIA sulfonate 1.5 hydrate.
Figure 3:
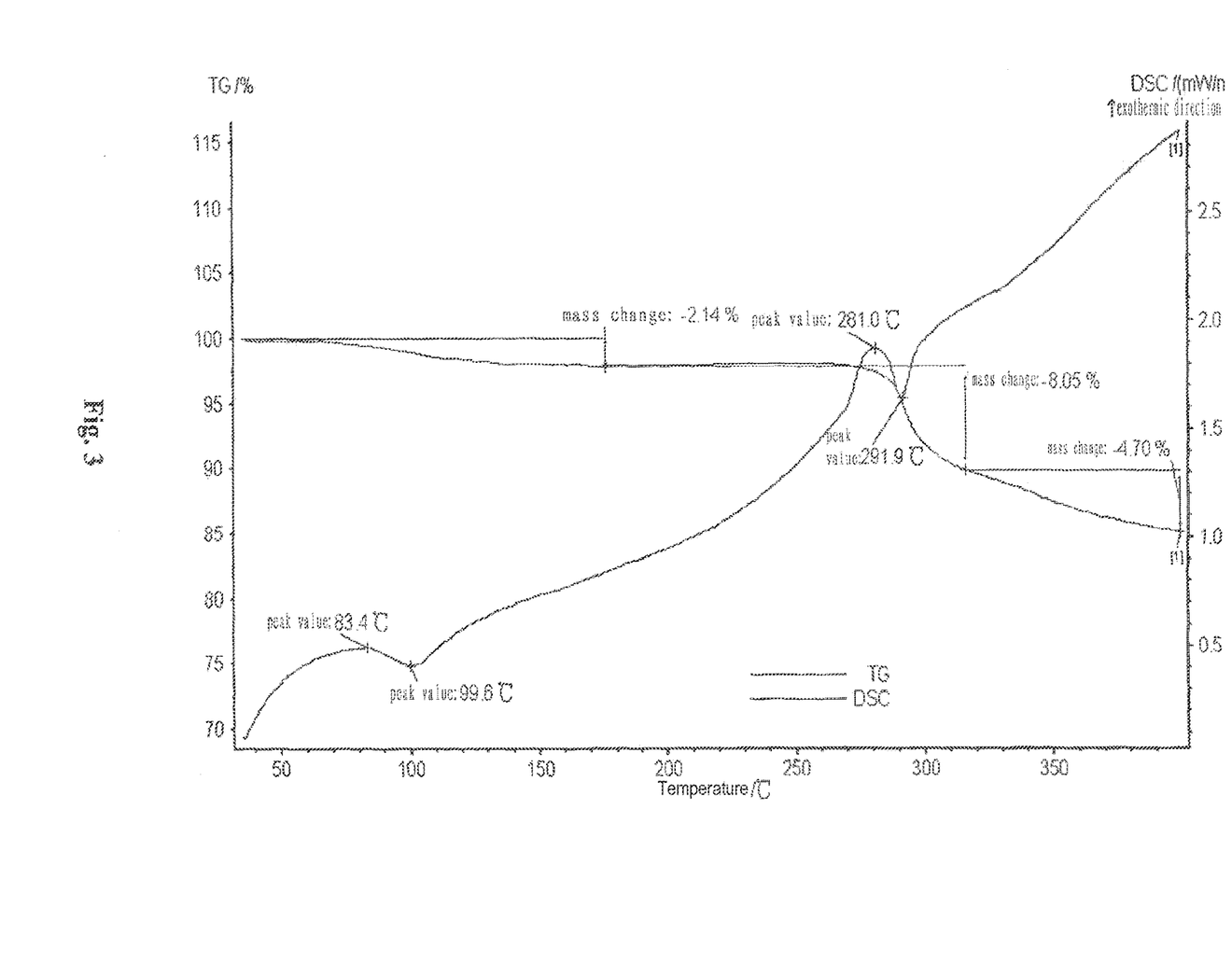
FIG. 3 is a thermogram of sodium tanshinone IIA sulfonate 0.5 hydrate.

Surprisingly, in distinctive, the hydrates of the present invention have corresponding endothermic peaks at weight-lose platform in thermograms (TG-DTA or TG-DSC), the thermograms indicate the crystalline hydrates of sodium tanshinone IIA sulfonate, such as 0.5 hydrate, 1.5 hydrate, 2.5 hydrate thereof, etc.

X-Ray Powder Diffraction Method

D/MX-IIIA X-ray diffractometer in the Material Testing Center of Wuhan University of Science and Technology was used to determine the X-ray diffraction patterns of sodium tanshinone IIA sulfonate hydrates with a diffraction angle 2θ scanning range of 3-80°.

Hygroscopicity Test

Samples of sodium tanshinone IIA sulfonate hydrates and anhydrous sodium tanshinone IIA sulfonate: anhydrous sodium tanshinone IIA sulfonate and the hydrates of the present invention, about 5 g for each, were placed in dry watch glass with constant weight, precisely weighed, subjected to the test at 25° C. and a relative humidity (RH) of 75%, separately sampled at 0 h and 48 h of the test, and the percentages of weight gain due to hygroscopicity was calculated. The results show that anhydrous sodium tanshinone IIA sulfonate has a hygroscopicity much higher than the sodium tanshinone IIA sulfonate hydrates of the present invention.

TABLE 1

Results of hygroscopicity test

| Sampling time (48 h) | Relative to 0 h, weight gain % |
|---|---|
| sodium tanshinone IIA sulfonate 2.5 hydrate | 1.25 |
| sodium tanshinone IIA sulfonate 1.5 hydrate | 4.12 |
| sodium tanshinone IIA sulfonate 0.5 hydrate | 7.96 |
| anhydrous sodium tanshinone IIA sulfonate | 11.43 |

Stability Test

Under RH75%, 30° C. and lucifuge condition, the samples of sodium tanshinone IIA sulfonate hydrate crystals and anhydrous sodium tanshinone IIA sulfonate were separately sealed in ampoules for accelerated stability test, chromatographic conditions: column Kromasil $C_{18}$ (250 mm×4.6 mm, 5 μm), mobile phase: methanol—0.02 mol/L potassium dihydrogen phosphate solution (adjusted with phosphoric acid to pH=4) (60:40), detection wavelength: 271 nm, flow rate: 1 ml/min, to measure increase extent of the relative substances (see results in Tables 1-2).

TABLE 2

Results of accelerated stability test

| Sampling time (6 month) | Relative to 0 month, multiple of the relative substances |
|---|---|
| sodium tanshinone IIA sulfonate 2.5 hydrate | 0.31 |
| sodium tanshinone IIA sulfonate 1.5 hydrate | 0.25 |
| sodium tanshinone IIA sulfonate 0.5 hydrate | 0.34 |
| anhydrous sodium tanshinone IIA sulfonate | 1.21 |

The results in the table confirm that the sodium tanshinone IIA sulfonate hydrate crystals of the present invention are much more stable than anhydrous sodium tanshinone IIA sulfonate.

EXAMPLE 1

Preparation of Sodium Tanshinone IIA Sulfonate 2.5 Hydrate 4 g of Tanshinone IIA (purchased from market), 30 ml of glacial acetic acid and 45 ml of acetic anhydride were placed in a dry three-necked flask, stirred for dissolution, added dropwise with 36 ml of a mixture solution of glacial acetic acid-concentrated sulfuric acid in volume ratio 1/1, reacted under stirring at 25° C. or below for 0.5-3 h, the reactant was slowly poured into water, added with 20 ml of saturated sodium chloride solution, filtered after solid precipitation completed, the precipitate was washed with saturated sodium chloride solution twice, washed with 95% cold ethanol twice, suction filtered, the solid was recrystallized with solvent of 5 ml of methanol, 12 ml of ethanol, 10 ml of chloroform, 20 ml of ethyl ether, 2 ml of water, placed at 0° C., suction filtered after crystal precipitation completed, the obtained solid was recrystallized again with solvent of 10 ml of methanol, 15 ml of chloroform, 15 ml of ethyl ether, 1 ml of water, placed at 0° C., suction filtered after crystal precipitation completed, the crystal was dried at about 50° C. for 6 h to obtain about 0.6 g of red crystal, melting point: 205-207° C. (ELECTROTHERMAL MELTING POINT APPARATUS, not calibrated); $\lambda^{H2O}_{max}$ 200, 228 nm, 256 nm, 271 nm; $^1$H-NMR (300 MHz, DMSO) δ7.86 (1H), δ7.57 (1H), δ3.08 (2H), δ2.33 (3H), δ1.73 (2H), δ1.62 (2H), δ1.29 (6H), the water peak at δ3.4 disappeared in $^1$H-NMR spectrum after heavy water exchange; $^{13}$C-NMR shows a total carbon number of 19, $^{13}$C-NMR (300 MHz, DMSO): δ182.9, δ175.9, δ158.7, δ154.6, δ150.1, δ143.5, δ134.1, δ127.6, δ127.1, δ120.6, δ120.3, δ117.5, δ38.0, δ35.0, δ32.1 (2↑C), δ30.2, δ19.4, δ10.0 (ppm); DEPT spectrum: 3 primary carbon atoms: δ32.1 (2 C), δ10.0; 3 secondary carbon atoms: δ38.0, δ30.2, δ19.4; 2 tertiary carbon atoms. ESI-MS: m/z: 396; EI: m/z: [M−Na] 373, [M+Na] 419; infrared spectrum: $v^{KBr}_{max}$ cm$^{-1}$ 3464 (wide), 2958, 2929, 2867, 1674, 1644, 1578, 1463, 1429, 1364, 1331, 1217, 1144, 1120, 1076, 1040, 923, 841, 709, 654; water content by Karl Fisher method was 10.46%, thermal analysis: platform weight lose was about 10.26%, this was in the error range of the result of sample containing 2.5 crystal water (theoretical value: 10.21%) (see: FIG. 1), elementary analysis, theoretical values: C, 51.70%; H, 5.02%; Na, 5.21%; S, 7.26%. measured values: C, 51.54%; H, 5.16%; Na, 5.08%; S, 7.39%.

EXAMPLE 2

Preparation of Sodium Tanshinone IIA Sulfonate 3 Hydrate

The above operation and steps were adopted, except that the crystallization solvent was changed as ethanol, chloroform, ethyl ether, water in a ratio similar to that of the above example, the crystal solid substance was dried at about 30° C. for 4 h to obtain 0.5 g of orange red crystal, melting point: 188-193° C. (not calibrated); $\lambda^{H2O}_{max}$ 200, 228 nm, 256 nm, 271 nm, ESI-MS: m/z: 396; EI: m/z: [M−Na] 373, [M+Na] 419; water content by Karl Fisher method was 14.07%, thermal analysis: platform weight lose was about 13.22% (theoretical value: 13.28%).

EXAMPLE 3

Preparation of Anhydrous Sodium Tanshinone IIA Sulfonate (Comparative Example)

The substance of Example 2 was vacuum dried at about 80° C. in the presence of $P_2O_5$ for 24-48 h or more to obtain an anhydrous substance thereof, and its water content by Karl Fisher method was lower than about 1.3% in general.

EXAMPLE 4

Preparation of Sodium Tanshinone IIA Sulfonate 1.5 Hydrate 4 g of Tanshinone IIA (purchased from market), 30 ml of propionic acid and 45 ml of propionic anhydride were placed in a dry three-necked flash, stirred, added dropwise with 36 ml of a mixture solution of glacial acetic acid-concentrated sulfuric acid in volume ratio 1/1, reacted under stirring at 25° C. or below for 0.5-3 h, the reactant was slowly poured into water, added with 75 ml of saturated sodium chloride solution, vacuum filtered after solid precipitation completed, the precipitate was washed with saturated sodium chloride solution twice, washed with 75% cold ethanol, suction filtered, the obtained solid was refluxed with anhydrous ethanol, suction filtered, the liquid was vacuum concentrated, the concentrated residue was recrystallized with 16 ml of methanol, 10 ml of chloroform, 25 ml of ethyl ether, 1.5 ml of water, 4 ml of acetone, placed at 0° C., suction filtered after precipitation completed, the obtained solid was recrystallized once again with a solvent in similar proportion, placed at 0° C., suction filtered after precipitation completed, the obtained solid was dried at about 60° C. for about 4 h to obtain about 0.5 g of red crystal, melting point: 214° C. decomposition (not calibrated); ultraviolet spectrum: 5 μg/ml water solution thereof was provided, measured according spectrophotometric method, maximum absorptions were at wavelengths of 200 nm, 228 nm, 256 nm and 271 nm, characteristic absorption was at 280 nm; Infrared spectrum: $v^{KBr}_{max}$ cm$^{-1}$ 3446 (wide), 2959, 2932, 2867, 1674, 1646, 1578, 1537, 1480, 1463, 1429, 1364, 1331, 1219, 1144, 1120, 1077, 1042, 923, 844, 709, 653; $^1$H-NMR (300 MHz, DMSO) δ7.84 (1H), δ7.54 (1H), δ3.06 (2H), δ2.34 (3H), δ1.72 (2H), δ1.62 (2H), δ1.29 (6H), the water peak of δ3.4 disappeared in $^1$H-NMR spectrum after heavy water exchange; $^{13}$C-NMR showed a total carbon number of 19, $^{13}$C-NMR (300 MHz, DMSO): δ182.8, δ175.7, δ158.6, δ154.6, δ150.0, δ143.4, δ134.0, δ127.6, δ127.1, δ120.6, δ120.3, δ117.5, δ38.0, δ35.0, δ32.1 (2↑C), δ30.1, δ19.3, δ10.0 (ppm); DEPT spectrum: 3 primary carbon atoms: δ32.1 (2 C), δ10.0; 3 secondary carbon atoms: δ38.0, δ30.1, δ19.3; 2 tertiary carbon atoms. ESI-MS: m/z: 396; EI: m/z: [M−Na] 373, [M+Na] 419; water content by Karl Fisher method was 6.62%, thermal analysis: platform weight lose was about 5.91%, this was in the error range of the result of sample containing 1.5 crystal water (theoretical value: 6.38%) (see: FIG. 2), elementary analysis, theoretical values: C, 53.90%; H, 4.76%; Na, 5.43%; S, 7.57%. measured values: C, 53.72%; H, 4.91%; Na, 5.27%; S, 7.43%. The X-ray powder diffraction pattern was shown in FIG. 5.

EXAMPLE 5

Preparation of Sodium Tanshinone IIA Sulfonate 0.5 Hydrate 3.5 g of Tanshinone IIA (purchased from market), 30 ml of propionic acid and 45 ml of propionic anhydride were placed in a dry three-necked flash, stirred, added dropwise with 36 ml of a mixture solution of propionic acid-concentrated sulfuric acid in volume ratio 1/1, reacted under stirring at 25° C. or below for 0.5-3 h, the reactant was slowly poured into water, slowly added dropwise with 5 ml of saturated sodium carbonate under stirring, then added with 60 ml of saturated sodium chloride solution, suction filtered after solid precipitation completed, the precipitate was washed with saturated sodium chloride solution twice, washed with 50% cold ethanol, suction filtered, the obtained crystal was refluxed with anhydrous ethanol, filtered, concentrated, the highly concentrated residue was crystallized with 15 ml of methanol, 20 ml of chloroform, 10 ml of ethyl ether, 1 ml of water, placed at 0° C., suction filtered after precipitation completed, the obtained solid was recrystallized once again with a solvent in similar proportion, placed at 0° C., suction filtered after precipitation completed, the obtained solid was dried in the presence of $P_2O_5$ at about 60° C. for about 6 h to obtain about 0.4 g of red crystal, melting point: 195-198° C. decomposition (not calibrated); ultraviolet spectrum: 5 μg/ml water solution thereof was provided, measured according spectrophotometric method, $\lambda^{H2O}_{max}$ 200 nm, 228 nm, 256 nm, 271 nm; $^1$H-NMR (300 MHz, DMSO) δ7.85 (1H), δ7.56 (1H), δ3.07 (2H), δ2.34 (3H), δ1.72 (2H), δ1.62 (2H), δ1.29 (6H), the water peak of δ3.4 disappeared in $^1$H-NMR spectrum after heavy water exchange; $^{13}$C-NMR showed a total carbon atoms of 19, $^{13}$C-NMR (300 MHz, DMSO): δ182.9, δ175.9, δ158.7, δ154.6, δ150.1, δ143.5, δ134.1, δ127.6, δ127.1, δ120.6, δ120.3, δ117.5, δ38.0, δ35.0, δ32.1 (2 C), δ30.2, δ19.4, δ10.0 (ppm); DEPT spectrum: 3 primary carbon atoms: δ32.1 (2 C), δ10.0; 3 secondary carbon atoms 3: δ38.0, δ30.2, δ19.4; 2 tertiary carbon atoms. ESI-MS: m/z: 396; EI: m/z: [M−Na] 373, [M+Na] 419; infrared spectrum: $v^{KBr}_{max}$ cm$^{-1}$ 3486 (wide), 2933, 1672, 1620, 1574, 1536, 1460, 1330, 1216, 1040, 922, 842, 656, water content by Karl Fisher method was 2.57%, thermal analysis TG-DSC: platform weight lose was about 2.14%, this was in the error range of the result of sample containing 0.5 crystal water (theoretical value: 2.22%) (see: FIG. 3); elementary analysis, theoretical values: C, 56.29%; H, 4.48%; Na, 5.67%; S, 7.91%. measured values: C, 56.15%; H, 4.62%; Na, 5.48%; S, 7.76%. The X-ray powder diffraction characteristics were shown in FIG. 4.

EXAMPLE 6

Preparation of Sodium Tanshinone IIA Sulfonate 1.5 Hydrate 4 g of Tanshinone IIA (purchased from market), 250 ml of dry dichloromethane and 50 ml of dry tetrachloroethane were placed in a three-necked flask, stirred for dissolution, added dropwise with 6.5 ml of chlorosulfonic acid (dissolving in 40 ml of dry dichloromethane in advance), reacted under stirring at 10° C. or below until the spots of reactant monitored by TLC disappeared, the reactant was slowly poured into 40 ml of water, the aqueous solution layer was separated, slowly added dropwise with saturated sodium carbonate solution under stirring until pH reached about 5, placed at 0° C. or below, suction filtered after precipitation completed, the obtained solid was crystallized with about 16 ml of methanol, about 10 ml of chloroform, about 25 ml of ethyl ether, about 1 ml of water, about 2 ml of acetone, placed at 0° C. or below, suction filtered after precipitation completed, the obtained solid was recrystallized once again with a solvent in similar proportion, placed at 0° C. or below, suction filtered after precipitation completed, the obtained solid was vacuum dried at about 60° C. for about 4 h to obtain about 0.2 g of red crystal, melting point: 212° C. decomposition (not calibrated); ultraviolet spectrum: 5 μg/ml water solution thereof was provided, measured according spectrophotometric method: $\lambda^{H2O}_{max}$ 200 nm, 228 nm, 256 nm, 271 nm; ESI-MS: m/z: 396; EI: m/z: [M−Na] 373, [M+Na] 419; $^1$H-NMR (300 MHz, DMSO) δ7.84 (1H), δ7.54 (1H), δ3.06 (2H), δ2.34 (3H), δ1.72 (2H), δ1.62 (2H), δ1.29 (6H), the water peak of δ3.4 disappeared in $^1$H-NMR spectrum after heavy water exchange; $^{13}$C-NMR showed a total carbon atom number of 19, $^{13}$C-NMR (300 MHz, DMSO): δ182.9, δ175.7, δ158.6, δ154.6, δ150.1, δ143.4, δ134.0, δ127.6, δ127.1, δ120.6, δ120.3, δ117.4, δ38.0, δ35.0, δ32.1 (2 C), δ30.1, δ19.3, δ10.0 (ppm); infrared spectrum: $v^{KBr}_{max}$ cm$^{-1}$ 3448 (wide), 2959, 2932, 2867, 1674, 1646, 1578, 1537, 1480, 1463, 1429, 1364, 1331, 1218, 1144, 1120, 1076, 1042, 923, 844, 709, 654; water content by Karl Fisher method was 6.57%, thermal analysis TG-DSC: platform weight lose was about 6.16%, this was in the error range relative to the theoretical value of 6.38%.

EXAMPLE 7

Manufacture of Sodium Tanshinone IIA Sulfonate Hydrate Froze-Dried Preparation 5 g of Sodium tanshinone IIA sulfonate 2.5 hydrate was added with 15 g of mannitol, 4 g of sodium dihydrogen phosphate, 2 g of sodium tartarate, 1 g of ascorbic acid, 0.02 g of EDTA disodium, about 800 ml of injection water at 30-50° C., stirred for dissolution, added with 1-5M citric acid and sodium hydroxide solutions to regulate pH as 4.0-7.0, supplemented with injection water to 1000 ml, added with activated carbon in an amount of 0.01-0.5% (W/V) and stirred for 15-30 min, filtered, filtered with 0.22 μm microporous membrane or filtered with ultrafiltration membrance with a molecular cut off of 6000-20000, the content of semi-finished product was measured, subpackaged in 5, 10 mg/bottle or 20 mg/bottle (expressed in anhydrous main drug), vacuum froze-dried, tamponed to obtain the froze-dried product.

EXAMPLE 8

Manufacture of Sodium Tanshinone IIA Sulfonate Hydrate Froze-Dried Preparation 10 g of Sodium tanshinone IIA sulfonate 1.5 hydrate or 0.5 hydrate was added with 20 g of sorbitol, 4 g of sodium dihydrogen phosphate, 2 g of sodium citrate, 0.02 g of EDTA disodium, about 800 ml of injection water at 30-50° C., stirred for dissolution, added with 1-5M citric acid and sodium hydroxide solutions to regulate pH as 5.0-7.5, supplemented with injection water to 1000 ml, added with activated carbon in an amount of 0.01-0.5% (W/V) and stirred for 15-30 min, filtered, filtered with 0.22 μm microporous membrane, the content of semi-finished product was measured, subpackaged in 10 mg/bottle or 20 mg/bottle or 40 mg/bottle (expressed in sodium tanshinone IIA sulfonate), vacuum froze-dried, tamponed to obtain the froze-dried product.

EXAMPLE 9

Manufacture of Sodium Tanshinone IIA Sulfonate Hydrate 5 g of Sodium tanshinone IIA sulfonate 2.5 hydrate or 1.5 hydrate or 0.5 hydrate (expressed in dry product) was added with 4 g of sodium gluconate, 2 g of sodium citrate, 1 g of ascorbic acid, 3 ml of propyl glycol, 0.06 g of EDTA disodium, added with injection water away from high light, fed with nitrogen gas, stirred for dissolution, added with 1-5M citric acid and sodium citrate solutions to regulate pH as 4.0-7.0, added with activated carbon in an amount of 0.01% (W/V), stirred for 15-45 min, filtered, supplemented with injection water to 2000 ml, filtered with 0.22 μm microporous membrane or ultrafiltration membrane with a molecular cut off of 6000-20000, the solution was fed with nitrogen gas for saturation, subpackaged in 10, 20 mg or 40 mg/bottle, sterilized to obtain the product.

EXAMPLE 10

Manufacture of Sodium Tanshinone IIA Sulfonate Hydrate 300 g of Glucose was weighed and added to injection water, stirred for complete dissolution, added with activated carbon in an amount of 0.5% relative to the amount of the formulated solution, heated for 10-30 min, filtered with sand filtration rod to remove carbon; 10 g of sodium tanshinone IIA sulfonate 1.5 hydrate was uniformly mixed with the above filtrate, added with 10 g of sodium dihydrogen phosphate, 2 g of sodium tartarate, 1 g of sulfobutyl-β-cyclodextrin, 0.1 g of EDTA disodium, stirred for dissolution, supplemented with injection water to 5000 ml, added with 1-3M hydrochloric acid or lactic acid or citric acid and sodium citrate solutions to regulate pH as 3.5-6.0, added with activated carbon in an amount of 0.05% relative to the amount of the formulated solution, heated and stirred for 10-30 min, filtered to remove carbon, then filtered once or twice with 0.22 μm microporous membrane or ultrafiltration membrane with a molecular cut off of 6000-20000, the solution was fed with high purity nitrogen gas for saturation, the semi-finished product was assayed in content, pH value and clarity, and the qualified solution was subpackaged in 10, 20 mg, 40 mg or 80 mg/bottle, sterilized to obtain the product.

EXAMPLE 11

Manufacture of Sodium Tanshinone IIA Sulfonate Hydrate Sodium Chloride Infusion 20 g of Sodium tanshinone IIA sulfonate 1.5 hydrate or 0.5 hydrate (expressed in anhydrous product), 425 g of sodium chloride, 5 g of sodium citrate, 5 g of tartaric acid, 0.6 g of EDTA disodium were added to injection water, the solution was fed with high purity nitrogen gas for saturation, stirred for complete dissolution, added with citric acid solution of sodium citrate solution to regulate pH as 3.5-6.5, added with injection water to 50000 ml, added with activated carbon in an amount of 0.05% relative to the formulated solution, heated and stirred for 10-30 min, filtered to remove carbon, filtered with 0.22 μm membrane or ultrafiltration membrane with a molecular cut off of 6000-20000, the semi-finished product was assayed in content, pH value and clarity, and subpackaged under high purity nitrogen gas atmosphere in 50 ml, 100 ml or 250 ml bottles or plastic bags, sterilized to obtain the product.

EXAMPLE 12

Sodium Tanshinone IIA Sulfonate Hydrate Tablets or Capsules (20 mg Per Tablet or Capsule Formulation:

| | |
|---|---|
| Sodium tanshinone IIA sulfonate 2.5 hydrate | 20 g |
| Microcrystalline cellulose | 65 g |
| Lactose | 10 g |
| Low-substituted hydroxypropylcellulose | 5 g |
| B-cyclodextrin | 5 g |
| 5% PVP-K30 (50% ethanol-water solution) | q.s. |
| Magnesium stearate | 2 g |

Sodium tanshinone IIA sulfonate 2.5 hydrate, microcrystalline cellulose, lactose, β-cyclodextrin, low-substituted hydroxypropylcellulose passed 100 mesh sieve, were added with an appropriate amount of 5% PVP-K30 50% ethanol-water solution as adhesive to form soft material, passed 18-24 mesh sieve, dried, passed 14-20 mesh sieve for trimming granules, mixed with magnesium stearate, filled in capsules or tableted.

EXAMPLE 13

Sodium Tanshinone IIA Sulfonate Hydrate Tablets or Capsules (50 mg Per Tablet or Capsule Formulation:

| | |
|---|---|
| Sodium tanshinone IIA sulfonate 1.5 hydrate | 50 g |
| Lactose | 165 g |
| Sodium carboxymethyl starch | 5 g |
| 5% PVP-K30 (50% ethanol-water solution) | q.s. |
| Magnesium stearate | 2 g |

Sodium tanshinone IIA sulfonate 1.5 hydrate, lactose, sodium carboxymethyl starch passed 100 mesh sieve, were added with an appropriate amount of 5% PVP-K30 50% ethanol-water solution as adhesive to form soft material, passed 18-24 mesh sieve to form granules, dried, passed 14-20 mesh sieve for trimming granules, mixed with magnesium stearate, filled in capsules or tableted.

EXAMPLE 14

Sodium Tanshinone IIA Sulfonate Hydrate Tablets or Capsules (100 mg Per Tablet or Capsule Formulation:

| | |
|---|---|
| Sodium tanshinone IIA sulfonate 0.5 hydrate | 100 g |
| Lactose | 155 g |
| Starch | 40 g |
| Low-substituted hydroxypropylcellulose | 5 g |
| 5% hydroxypropylmethyl cellulose 50% ethanol-water solution | q.s. |
| Magnesium stearate | 2 g |

Sodium tanshinone IIA sulfonate 0.5 hydrate, microcrystalline cellulose, lactose, low-substituted hydroxypropylcellulose passed 100 mesh sieve, were added with an appropriate amount of 5% hydroxypropylmethyl cellulose 50% ethanol-water solution as adhesive to form soft material, passed 18-24 mesh sieve to form granules, dried, passed 14-20 mesh sieve for trimming granules, mixed with magnesium stearate, filled in capsules or tableted.

EXAMPLE 15

Manufacture of Sodium Tanshinone IIA Sulfonate Hydrate Granules

Including: granules of sodium tanshinone IIA sulfonate 4 hydrate or sodium tanshinone IIA sulfonate 3 hydrate or sodium tanshinone IIA sulfonate (50 mg per bag)
Formulation:

| | |
|---|---|
| Sodium tanshinone IIA sulfonate hydrate | 50 g (expressed in anhydrous product) |
| Mannitol | 155 g |
| Lactose | 20 g |
| Solid edible essence | 1 g |
| 5% hydroxypropylmethylcellulose | q.s. |

Sodium tanshinone IIA sulfonate hydrate, mannitol, lactose, edible essence passes 100 mesh sieve, added with an appropriate amount of 5% hydroxypropylmethyl cellulose 50% ethanol-water solution as adhesive to form soft material, passed 18-24 mesh sieve to form granules, dried at 60° C. or below, passed 14-20 mesh sieve for trimming granules, sub-packaged.

EXAMPLE 16

Pharmacological Test

1. Effects on Arrhythmia Induced by Calcium Chloride in Rats

50 SD rats were provided, male and female, body weight 226±31 g, randomly divided into 5 groups, separately administered by intravenous injection with physiological saline, Quinidine, sodium tanshinone IIA sulfonate hydrate (dissolved in physiological saline) 6 $mg \cdot kg^{-1}$. The rats were anaesthetized with 3% pentobarbital sodium 40 $mg \cdot kg^{-1}$, fixed in supine position on operation table, injected via lingual vein for 6 minutes, quickly intravenously injected (completed injection in 5 s) with 2.5% calcium chloride 100 $mg \cdot kg^{-1}$ (0.4 ml/100 g), the number of animal with ventricular fibrillation and the number of died animals were recorded.

The results show that in the sodium tanshinone IIA sulfonate hydrate groups, ventricular fibrillation induced by calcium chloride in rats can be significantly inhibited ($p<0.05$), and in the sodium tanshinone IIA sulfonate hydrate groups, the arrhythmic death induced by calcium chloride in rats can be significantly inhibited (Table 3).

TABLE 3

Effects of sodium tanshinone IIA sulfonate hydrate on arrhythmia induced by calcium chloride in rats

| Drug | Dose ($mg \cdot kg^{-1}$) | Animal number (n) | Arrhythmic animal number (n) Ventricular fibrillation | Heart arrest |
|---|---|---|---|---|
| Physiological saline | 5 $ml \cdot kg^{-1}$ | 10 | 10 | 10 |
| Quinidine | 13.5 | 10 | 6 | 4 |
| 2.5 Hydrate of the invention | 10 | 10 | 6 | 5 |
| 1.5 Hydrate of the invention | 10 | 10 | 5 | 6 |
| 0.5 Hydrate of the invention | 10 | 10 | 5 | 4 |

2. Effects on Rat Ischemic Reperfusion

36 Male Wistar rats, body weight 250-300 g, were randomly divided into 3 groups: sham operation group, ischemic reperfusion group, and group of drug of the invention, 12 rats per group. As for group of drug of the invention: the rats were peritoneally administered with sodium tanshinone IIA sulfonate 1.5 hydrate in physiological saline, does of 40 mg/kg, twice per day, for consecutive 7 days, and subjected to cerebral ischemia operation 60 min after the last administration; the rats of sham operation group and ischemic reperfusion group were administered with the same volume of isometric physiological saline, respectively.

The rats were anesthetized with 10% chloral hydrate (3.5 ml/kg) by peritoneal injection, fixed in supine position, modeled by the improved Zea Longa thread occlusion method in document [Journal of Shanghai Jiaotong University (Medicine), 2007, 27(10):1218-1222]; in the sham operation group, thread was merely inserted 10 mm, and other steps were the same as the model group, animals appeared operation-side Horner syndrome and opposite-side movement disorder were deemed as successfully established models. After successful establishment of models, the animals were administered in the same dose as above twice per day, and the sham operation group and ischemic reperfusion group were administered with the same volume of isometric physiological saline, respectively. The thread was drawn out 2 h after model establishment, the rats were executed 24 h after reperfusion, their brains were taken out quickly and weighed. Physiological saline was used to prepare 10% brain tissue homogenate solution at low temperature, centrifuged at low temperature, 3000 r/min for 10 min, the deposit was discarded, the supernatant was taken up and tested to determine SOD, MDA, NO, NOS contents or activities according to the specifications of the corresponding commercial SOD, MDA, NO, NOS kits, the results are shown in Table 4.

TABLE 4

Effects of drug of the invention on NO, NOS, MDA, SOD in ischemic reperfusion brain tissues of rats

| Group | NO (μmol/L) | NOS (U/ml) | MDA (nmol/ml) | SOD (U/ml) |
|---|---|---|---|---|
| Sham operation | 22 ± 6.41 | 18 ± 5.14 | 1.56 ± 0.47 | 279 ± 22.62 |
| Ischemic reperfusion | 31 ± 7.47 | 29 ± 5.78 | 3.73 ± 0.59 | 218 ± 21.77 |
| Drug of the invention | 24 ± 6.35 | 22 ± 5.31 | 2.26 ± 0.62 | 245 ± 21.59 |

The results show that in compared to the sham operation group, the SOD activity in brain tissue of rats of the ischemic reperfusion group decreased significantly, and MDA, NO content and NOS activity increased significantly ($P<0.01$); in compared to the ischemic reperfusion group, group of drug of the invention had a significantly increase in SOD activity, a decrease in NOS activity, and a significant decrease in MDA and NO content in brain tissues of rats ($P<0.01$). When the sodium tanshinone IIA sulfonate 0.5 hydrate and sodium tanshinone IIA sulfonate 2.5 hydrate of the present invention were separately subjected to the above ischemic reperfusion test, the results similar to those of the sodium tanshinone IIA sulfonate 1.5 hydrate were obtained. These results confirm that the present drugs provide protection effects on cerebral ischemic reperfusion injury by regulating NOS activity and NO content.

3. Protection Effects on Calcium Paradox Cardiac Muscle

Cardiac muscle calcium paradox models were established by building ex vivo heart perfusion in guinea pigs by referring to the document (Edited by XU Shuyun, et al., Pharmacological Test Method, $3^{rd}$ edition, p 986-1000; Chinese Journal of Pathophysiology, 1987, 3:154-158). 48 Healthy guinea pigs, body weight 280-360 g, were divided into 6 groups, 8 guinea pigs per group, separately comprising: normal control group, calcium paradox group, iproveratril positive control group, 3 drug-administrated groups, the animals were fasted for one night before test, intraperitoneally injected with heparin 0.5 mg/kg, intraperitoneally injected with pentobarbital sodium 30 mg/kg after 20 min, their chests were opened after anesthesia, and hearts were taken out quickly, immersed in Kreb's-Henseleit (K-H) perfusion solution as cooled with ice, after aortic cannulation, the hearts were placed in ex vivo heart perfusion device with constant temperature and constant pressure. Referring to the document (Chinese Journal of Pathophysiology, 1987, 3:154-158), the hearts were perfused by Langendorff method at 37° C., in which the 3 drug-administrated groups were subjected to calcium paradox plus the compound of the present invention 32 mg/L, the normal control group was subjected to a continuous perfusion for 35 min with calcium-containing Kreb's-Henseleit solution, the effluent of coronary artery of the last 20 min was collected, the other 5 groups were subjected to a perfusion for 10 min with calcium-containing K-H solution to reach stable state of heart, perfusion for 5 min with calcium-free K-H solution, then perfusion for 20 min with calcium-containing K-H solution again, so that calcium paradox models were established by such perfusion procedure, in which the positive control group was subjected to perfusion solution with 2.1 mg/L iproveratril in whole procedure, and the drug-administrated groups were subjected to perfusion solutions to which 32 mg/L sodium tanshinone IIA sulfonate hydrate was added separately. The effluent of coronary artery of 20 min when calcium-containing perfusion solution was restored was collected, the protein release amounts mg/min/g drywt and cardiac muscle tissue calcium uptake μmol/g drywt in the collected coronary artery effluents were measured according to the reference document. It is found that the result differences from the drug-administrated groups are significant ($P<0.01$) compared with the calcium paradox group, see Table 5 and Table 6.

TABLE 5

Effects of the compound of the invention on protein release amount in calcium paradox cardiac muscle tissue

| Group | Number of guinea pigs per group | Dose | Protein release, $\bar{x} \pm S$ mg/min/g, dry weight | Protein release decrease rate, % |
|---|---|---|---|---|
| Normal control | 8 | | 0.5 ± 0.1 | |
| Calcium paradox | 8 | | 5.0 ± 0.4 | 0 |
| Iproveratril | 8 | 2.1 mg/L | 2.6 ± 0.2 | 48% |
| 2.5 Hydrate of the invention | 8 | 32 mg/L | 2.5 ± 0.2 | 50% |
| 1.5 Hydrate of the invention | 8 | 32 mg/L | 2.4 ± 0.3 | 52% |
| 0.5 Hydrate of the invention | 8 | 32 mg/L | 2.4 ± 0.2 | 52% |

TABLE 6

Effects of the compound of the invention on calcium uptake in calcium paradox cardiac muscle tissue

| Group | Number of guinea pigs per group | Dose | Calcium uptake, $\bar{x} \pm S$ μmol/min/g, dry weight | Calcium uptake decrease rate, % |
|---|---|---|---|---|
| Normal control | 8 | | 15.7 ± 1.3 | |
| Calcium paradox | 8 | | 47.6 ± 3.7 | 0 |
| Iproveratril | 8 | 2.1 mg/L | 36.9 ± 2.5 | 22.5% |
| 2.5 Hydrate of the invention | 8 | 32 mg/L | 35.4 ± 3.1 | 25.6% |
| 1.5 Hydrate of the invention | 8 | 32 mg/L | 35.2 ± 2.8 | 26.1% |
| 0.5 Hydrate of the invention | 8 | 32 mg/L | 34.5 ± 2.4 | 27.5% |

It can be seen that the compound of the inventions have significant protection effects on cardiac muscle calcium paradox injury, have calcium ion antagonism, can inhibit calcium influx, and reduce the cardiac muscle tissue calcium deposition during calcium paradox procedure and the protein release caused by cardiac muscle injury.

It can be understood in the art that many changes of detains are possible, which do not limit the spirit and the scope of the present invention, and the present invention is not limited to the above examples.

What is claimed is:

1. A sodium tanshinone IIA sulfonate hydrate, which molecular formula is $C_{19}H_{17}NaO_6S \cdot nH_2O$, wherein n=2.5, characterized in that by using X-ray powder diffraction method to measure within the range of diffraction angle 2θ (3-80°), the hydrate has corresponding characteristic values at the following 2θ: about 3.7, 4.3, 6.2, 7.3, 8.8, 9.3, 11.5, 14.7, 15.4, 17, 17.7, 21.2, 25.9, 27.3, 27.6, 29.4.

2. A sodium tanshinone IIA sulfonate hydrate, which molecular formula is $C_{19}H_{17}NaO_6S \cdot nH_2O$, wherein n=1.5, characterized in that by using X-ray powder diffraction method to measure within the range of diffraction angle 2θ (3-80°), the hydrate has corresponding characteristic values at the following 2θ: about 3.7, 6.2, 7.3, 8.8, 9.2, 11.5, 14.7, 15.4, 17, 17.7, 20.6, 21.2, 25.9, 27.1, 27.6, 29.4.

3. A sodium tanshinone IIA sulfonate hydrate, which molecular formula is $C_{19}H_{17}NaO_6S \cdot nH_2O$, wherein n=0.5, characterized in that by using X-ray powder diffraction method to measure within the range of diffraction angle 2θ (3-80°), the hydrate has corresponding characteristic values at the following 2θ: about 3.7, 7.6, 9.0, 9.6, 15.3, 22.0, 26.0, 27.6, 29.8.

Figure 5:
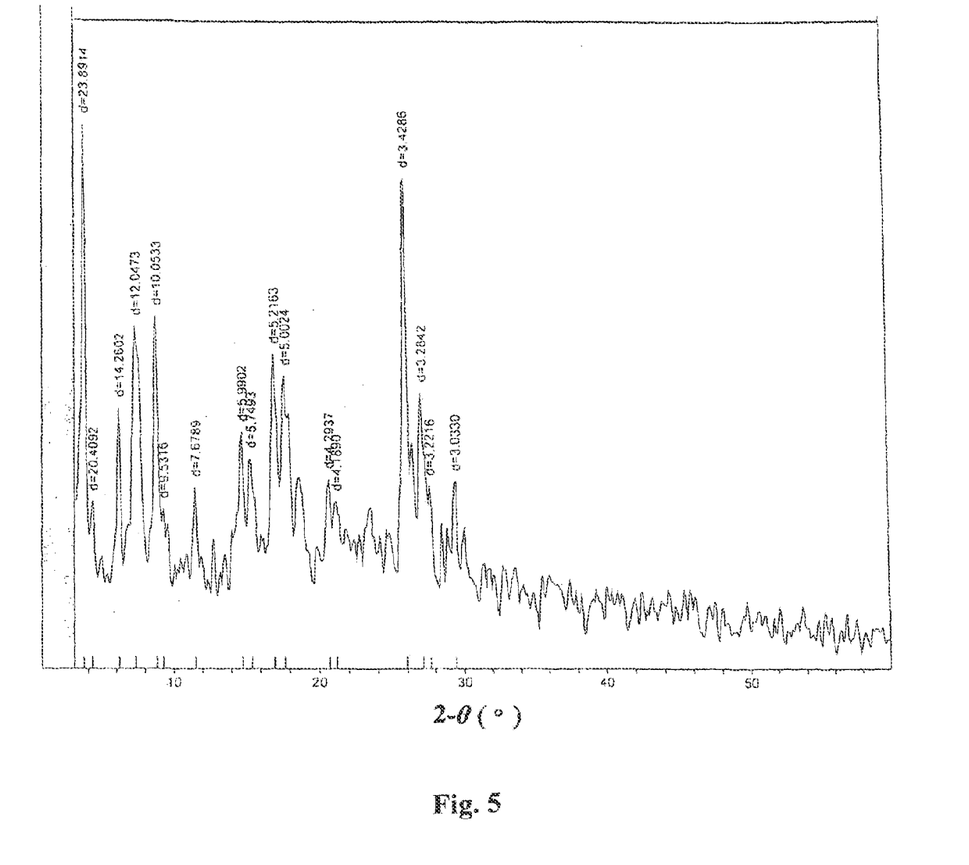
FIG. 5 is an X-ray powder diffraction pattern of sodium tanshinone IIA sulfonate 1.5 hydrate.

4. The sodium tanshinone IIA sulfonate hydrate according to claim 2, characterized in that by using X-ray powder diffraction method to measure within the range of diffraction angle 2θ (3-80°), the hydrate has the X-ray powder diffraction characteristics as shown in FIG.5.

Figure 4:
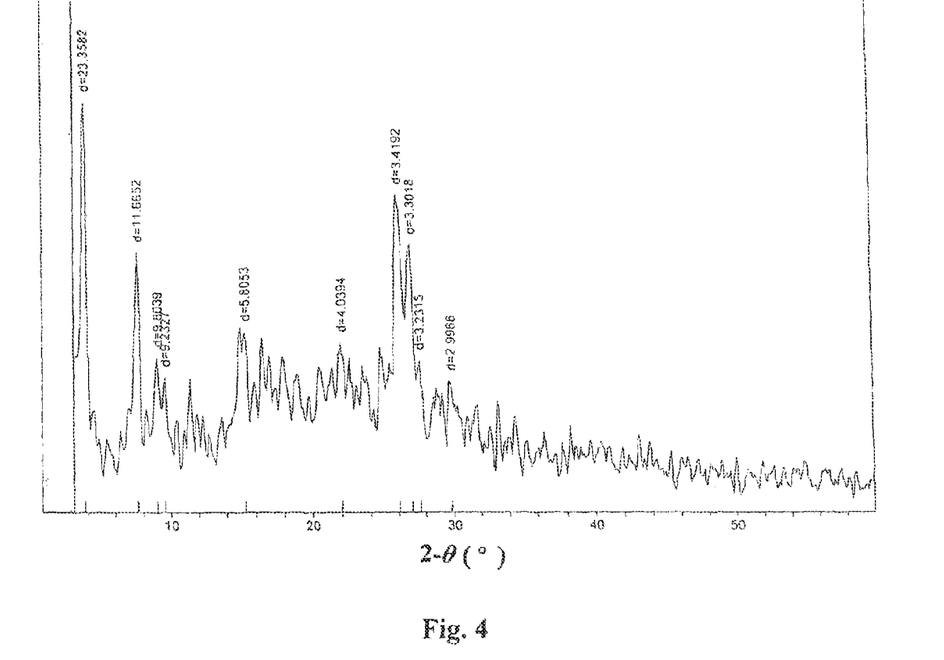
FIG. 4 is an X-ray powder diffraction pattern of sodium tanshinone IIA sulfonate 0.5 hydrate.

5. The sodium tanshinone IIA sulfonate hydrate according to claim 3, characterized in that by using X-ray powder diffraction method to measure within the range of diffraction angle 2θ (3-80°), the hydrate has the X-ray powder diffraction characteristics as shown in FIG.4.

6. A method for preparing sodium tanshinone IIA sulfonate hydrate, which molecular formula is $C_{19}H_{17}NaO_6S \cdot nH_2O$, wherein n=0.5-4.0, the method comprising:

Method A:
  placing tanshinone IIA in a reaction container;
  adding one or more of acetic acid, acetic anhydride, propionic acid, propionic anhydride and C1-C6 low hydrocarbons substituted with halogen;
  stirring;
  adding one or more of solutions of acetic acid, acetic anhydride, propionic acid and propionic anhydride in sulfuric acid or fuming sulfuric acid or chlorosulfonic acid;
  after the end of dropwise adding, stirring at 30° C. for 0.1-6 h;
  slowly pouring the reactant into water, adding one or more of solutions of sodium chloride, sodium carbonate, sodium bicarbonate and sodium hydroxide;
  precipitating sufficiently;
  filtering;
  washing the precipitate once or several times with saturated sodium chloride solution or saturated sodium sulfate solution;
  then washing once or several times with water or C1-C6 low molecular weight alcohols or combination thereof;
  filtering;
  subjecting the resultant solid to crystallization with one or more solvent(s) selected from the group consisting of water, C1-C6 low hydrocarbons substituted with halogen, C2-C6 low ethers and aromatic hydrocarbons;
  cooling;
  standing;
  filtering after crystal precipitation;
  drying to obtain sodium tanshinone IIA sulfonate hydrate crystal; and
  purifying the product; or Method B:
  placing tanshinone IIA in a reaction container;
  adding one or more of acetic acid, acetic anhydride, propionic acid, propionic anhydride and C1-C6 low hydrocarbons substituted with halogen;
  stirring;
  adding a chlorosulfonic acid solution in one or more of C1-C6 low hydrocarbons substituted with halogen;
  after the end of dropwise adding, stirring at 30° C. for 0.1-6 h;
  slowly pouring the reactant into water;
  separating organic layer;
  adding a saturated solution of one or more of sodium chloride, sodium carbonate, sodium bicarbonate, sodium hydroxide to the resultant aqueous solution layer;
  standing;
  precipitating sufficiently;
  filtering;
  washing the precipitate once or several times with saturated sodium chloride solution or saturated sodium sulfate solution;
  then washing once or several times with one or more of water or C1-C6 low molecular weight alcohols or combination thereof;
  subjecting the resultant solid to crystallization with one or more solvent(s) selected from the group consisting of water, C1-C6 low molecular weight alcohols, C3-C6 low ketones, C2-C8 low esters, C1-C6 low hydrocarbons substituted with halogen, C2-C6 low ethers and aromatic hydrocarbons;
  standing;
  cooling;
  filtering after crystal precipitation; and
  drying to obtain sodium tanshinone IIA sulfonate hydrate crystal.

7. The method according to claim 6, wherein the one or more solvent(s) used for crystallization is/are selected from the group consisting of water, methanol, ethanol, isopropanol, acetone, butanone, hexone, methyl acetate, ethyl acetate, dichloromethane, chloroform, ethyl ether and benzene.

8. A pharmaceutical composition, comprising the sodium tanshinone IIA sulfonate hydrate according to claim 1, and a pharmaceutically acceptable carrier.

9. The pharmaceutical composition according to claim 8, wherein the pharmaceutical composition is processed to form froze-dried powders aseptically subpackaged powders, infusion solutions, small volume injections, or oral preparations.

10. A pharmaceutical composition, comprising the sodium tanshinone IIA sulfonate hydrate according to claim 2, and a pharmaceutically acceptable carrier.

11. The pharmaceutical composition according to claim 10, wherein the pharmaceutical composition is processed to form froze-dried powders, aseptically subpackaged powders, infusion solutions, small volume injections, or oral preparations.

12. A pharmaceutical composition, comprising the sodium tanshinone IIA sulfonate hydrate according to claim 3, and a pharmaceutically acceptable carrier.

13. The pharmaceutical composition according to claim 12, wherein the pharmaceutical composition is processed to form froze-dried powders, aseptically subpackaged powders, infusion solutions, small volume injections, or oral preparations.

14. A method for treating or preventing cerebral ischemic reperfusion injury in humans and mammals, the method comprising:
   administrating the sodium tanshione IIA sulfonate hydrate according to claim 1 to patients and mammals in need thereof.

15. A method for treating or preventing cerebral ischemic reperfusion injury in humans and mammals, the method comprising:
   administrating the sodium tanshione IIA sulfonate hydrate according to claim 2 to patients and mammals in need thereof.

16. A method for treating or preventing cerebral ischemic reperfusion injury in humans and mammals, the method comprising:
   administrating the sodium tanshione IIA sulfonate hydrate according to claim 3 to patients and mammals in need thereof.

\* \* \* \* \*